United States Patent [19]

Qu et al.

[11] Patent Number: 5,290,784

[45] Date of Patent: Mar. 1, 1994

[54] ACONITANE DERIVATIVES USED AS A MEDICATION TO TREAT ADDICTION

[75] Inventors: Yueqian Qu; Peng Qu, both of Lanzhou, China

[73] Assignee: Yueqian Qu, Lanzhou, China

[21] Appl. No.: 912,791

[22] Filed: Jul. 13, 1992

[30] Foreign Application Priority Data

Jul. 18, 1991 [CN] China .................... 91104811.1

[51] Int. Cl.$^5$ .................................................. A61K 31/44
[52] U.S. Cl. ................................. 514/279; 514/810; 514/812
[58] Field of Search ............... 514/216, 279, 289, 810, 514/812

[56] References Cited

U.S. PATENT DOCUMENTS

| | | | |
|---|---|---|---|
| 4,012,505 | 3/1977 | Boici | 424/195.1 |
| 4,352,796 | 10/1982 | Arichi et al. | 424/195.1 |
| 4,656,178 | 4/1987 | Junusov et al. | 514/279 |

Primary Examiner—S. J. Friedman
Assistant Examiner—William Jarvis
Attorney, Agent, or Firm—McAulay Fisher Nissen Goldberg & Kiel

[57] ABSTRACT

This invention relates to a medication to treat addicts who are addicted to drugs or narcotics (including opium, morphine, heroine, cocaine, marijuana, amphetamine, etc.), the preparative method of this medication, as well as the treatment method for the addicts by using this medication. This medication to treat addiction is aconitane deivative having structures of formula I or II, wherein the formula I, $R=\alpha$—$OCH_3$, $\beta$—$OCH_3$ or $\alpha$—OH; $R_1$=OAcABz, OH, OABz or H; $R_2$=H or OH; $R_3$=H or OH; $R_4$=H or OH; $R_5$=H or OH; $R_6$=$OCH_3$, OBz, OAc or OH; wherein the formula II, $R_1$=$R_2$=$R_3$=OH.

This medication to treat addiction is characterized by no drug-dependence, high cure effect, fast action and low side effect.

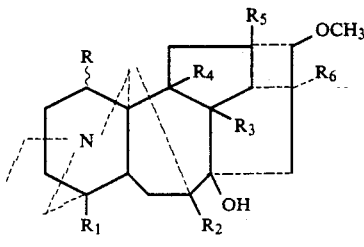

or

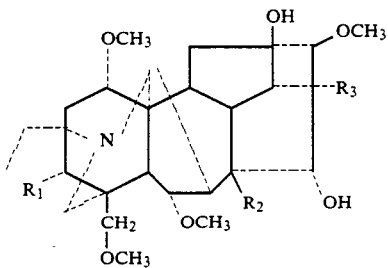

18 Claims, 1 Drawing Sheet

FIG. 1

ACONITANE DERIVATIVES USED AS A MEDICATION TO TREAT ADDICTION

This invention relates to the aconitane derivatives used as medication to treat addicts dependent upon drugs or narcotics. In another aspect this invention relates to the preparative method of this medication. In yet another aspect this invention relates to the method to treat addiction by using this medication.

In this invention, the term "medication to treat addiction" means that a medicament which can relieve the drug dependence or narcotic dependence for those who are addicted to drugs or narcotics, and cure the withdrawal syndrome caused by continuing use of drugs.

In this invention, the term "dependence" means a physical (physiologic) or physical (psycologic) dependence upon drugs, as evidenced by forced abuse of drugs or narcotics without medicinal purpose, to achieve the desired effect, or to avoid withdrawal symptoms when the drugs were discontinued or reduced in amount.

In this invention, the term "drug" means a substance which may make a person dependent upon it after continuous use, for example, opium, morphine, heroin, cocaine marijuana, as well as amphetamine, etc.

In this invention, the term "withdrawal syndrome" means symptoms such as perspiration, lacrimation, yawing, chilling, getting goose flesh, mydriasis, vomiting, diarrhea, abdominalgia, arrbythmia, blood pressure increase, insomnia, furor and tremor, etc. This syndrome results in the vigorous physical reaction of those who have stopped using drugs or narcotics on which they have become dependent.

It is reported that all over the world there are some 40 million drug addicts, and the volume of drug trade is estimated to be $5,000 billion per year. On the one hand, drug abuse brings serious damage to the human psyche and body, for example, loss of moral integrity, decrease of health level, shortening life, serious withdrawal syndrome after discontinuing the drugs, sometimes even endangering life; on the other hand, drug abuse brings about unstability in the society because the drug abusers always act unscrupulously to get drugs and become a main source of serious crime in the society. Consequently, drug abuse has seriously imperiled the progress and safety of human society. To counter the drug abuse becoming increasingly serious, governments all over the world have adopted a policy and measures to strictly prohibit drug abuse. However, this problem is still growing and spreading. Therefore, ahead of human society lies an urgent mission to seek medication and methods with a high cure effects and low side effect in order to control and treat drug addiction.

At present, the major methods of treatment for addiction in most countries are as follows:

1. Reducing Regimen

The main composition of the medication used in the method is opium. At different stages of the treatment, the opium content is decreased successively until it is zero. The drug abuser is cured in this way.

2. Substitution Method

Analgesic methadone is used to treat the drug abuser in this method.

Medical practice shows that serious drawbacks occurs with both the above treatments for addiction. For example, the former requires a long period of treatment. Furthermore, this method cannot make the drug addicts radically relieve this dependency upon drugs once and for all, and the proportion of reabuse after treatment is high. In the later method, methadone may also produce drug dependence, for example, dependence potential of 100 mg of oral methadone is equivalent to that of 10 mg of injected morphine. Meanwhile, methadone itself has many adverse reactions such as pneumonectasis, immunologic symptoms, impotency, as well as accumulation in body leading to intoxication, and more seriously, blindness in both eyes. Furthermore infants born by mothers addicted to methadone are likely to show withdrawal symptoms. Consequently, the substitution method is not an ideal treatment for addiction either.

At present, there are many medications being tested to treat addiction, for example: Abbott 69024, Amantidine, Bupropion, Buprenorphine, Bromocriptine, Buspirone, Carbamazepine (Tegretol), Fluoxetine (Prozac), Flupenthixol, Gepirone, LAAM, Mazindol, Naltrexone and Schering 23390 (see ref: Scientific American, March 1991, pp94–103). While very few of them have been proved ineffective others are being under investigation. Thus, there is an urgent need for a drug-independent medication of high curative effect and low side effect for treatment of addiction.

The object of this invention is to find medications to treat addiction and a treatment method without drug dependence and with a high cure effect and low side effect.

After broad investigation, the inventor has found that the aconitane derivatives which have the structures of formula I/II and their inorganic acid salts possess excellent effects of treating addiction without drug dependence:

In formula I, $R = \alpha\text{—OCH}_3$, $\alpha\text{—OH}$ or $\beta\text{—OCH}_3$, $R_1 = \text{OAcABz}$, OH, OABz or H; $R_2 = $ H or OH; $R_3 = $ H or OH; $R_4 = $ H or OH; $R_5 = $ H or OH; $R_6 = \text{OCH}_3$, OBz, OAc or OH; $Ac = \text{—COCH}_3$;

In formula II, $R_1 = R_2 = R_3 = OH$.

The inventor has also found that treating the drug addict with the aconitane derivative of this invention can relieve the drug dependence and completely cure withdrawal syndrome within 3~4 days. The medication from this invention exhibits drug independence and low side effect. Based on the above discovery, the inventor has completed this invention.

One of the subjects of this invention relates to the aconitane derivatives of following structures (Formula I or II), which can relieve the addicts dependence upon drugs or narcotics as well as the withdrawal symptoms when the substances are discontinued.

The medication made by this invention may or may not contain anticholinergic agents such as scopolamine hydrobromide, or anisodamine hydrobromide. The aconitane derivatives used as medication treating addiction in this invention are listed in tables 1 and 2.

According to this invention, the medication to treat addiction can be used in the form of aconitane derivative having the structure of either formula I or II, or their inorganic acid salts, or their mixture. Also, the medication can be used in the form of mixture of each of three of the foregoing with anticholinergic agents such as scopolanisne, or anisodamine, or their inorganic acid salts as well as medical excipients.

According to this invention, the preferred medication composition to treat addiction is either the lappaconitine or its inorganic salts, the total alkaloids of *Aconitum sinomontanum* Nakai or its inorganic acid salts, N-deacyl-lappaconitine or its inorganic acid salts, or the mixture of each from three of the foregoing with anticholinergic agents such as scopolamine hydrobromide as well as the excipient.

Another subject of this invention relates to a preparative method of aconitane derivatives having structures of formula I or II:

or

In formula I, $R = \alpha-OCH_3$, $\alpha-OH$ or $\beta-OCH_3$; $R_1 = OAcABz$, OH, OABz or H; $R_2 = H$ or OH; $R_3 = H$ or OH; $R_4 = H$ or OH; $R_5 = H$ or OH; $R_6 = OCH_3$, OBz, OAc or OH; $Ac = -COCH_3$;

In formula II, $R_1 = R_2 = R_3 = OH$;

The preparative method comprises:

1) Lappaconitine and its inorganic acid salts were extracted, separated and prepared from the roots of a Ranunculaceae plant, *Aconitum sinomontanum* Nakai;

2) Total alkaloids of *A. sinomantanum* and its inorganic acid salts were extracted, separated and prepared from the roots of *Aconitum sinomontanum* Nakai by using an ion-exchange resin method or 3) Aconitane derivatives and its inorganic acid salts was prepared by semi-synthesis from pure compound of aconitane derivatives.

In the above item 1), the detailed description of production of lappaconitine and its inorganic acid salts is as follows:

The root of *Aconitum sinomontanum* Nakai were ground to a powder which was placed in a reflux extractor and soaked in 95% ethanol at room temperature overnight. The mixture was heated and refluxed until the extract did not indicate an alkaloid reaction against Dragendorff reagent. The extract was concentrated by heating under reduced pressure. The concentrate was dissolved by adding 2% hydrochloric acid, and then filtered. The filtrate was alkalized (PH=9) by adding concentrated ammonia, then extracted with dichloromethane or chloroform until the extract did not indicate alkaloid reaction against Dragendorff reagent. The extracts were combined, and then filtered. The filtrate was concentrated by heating under reduced pressure to give a residue which was dissolved in anhydrous ethanol. The solution was allowed to stand and gave a crystalline product, lappaconitine. The produce was collected by filtration. After recrystallization with ethanol or acetone, white lappaconitine crystalline was obtained.

To the methanol-acetone solution of the obtained lappaconitine, a solution of hydrobromic acid in ethanol was added dropwise until the Cougo red paper indicated blue color when testing the solution.

To the solution, ether was then added dropwise to cloudiness. The solution was allowed to stand to give crystals which were collected by filtration and dried to give lappaconitine hydrobromide.

In the above item 2), the preparation of total alkaloids of *A. sinomantanum* and their inorganic acid salts was carried out as follows:

The roots of *Aconitum sinomontanum* Nakai were ground to a powder, and then percolated with 0.05N hydrochloric acid until the percolate indicated no alkaloid reaction against Dragendorff. reagent. The 15-fold percolate by weight based on the weight of root powder was collected. A column was packaged with 1/5 polystyrene resin by weight based on the weight of the root powder (sulfonic acid functionality, H-type, cross-linking degree 4%). The collected percolate passed the column at speed of 600~800 ml/hr. Once all the percolate went through the column, the resin was poured into a container and washed with distilled water to remove the suspended solid impurities. After being drying in air, the resin was alkalized by adding ammonia (10%), then placed in a reflux extractor to be extracted with dichloromethane or chloroform until the extract indicated no alkaloid reaction against Dragendorff reagent. The extract was filtered and the filtrate was concentrated to dryness. The resulting material was dissolved in ethanol or acetone by warming. The solution was allowed to stand and gave white crystal. The total alkaloids of *A. sinomontanum* was obtained by filtration and recrystalization from ethanol or acetone. Its hydrobromide was prepared by the same method as described in 1).

In the above item 3), the certain pure compound of aconitane derivatives from this invention was prepared by semi-synthesis scheme which is as follows:

Semi-synthesis scheme:

Delavaconine

Aconitine

Aconine

Episcopalisine

Episcopalisinine

Another subject of this invention relates to a preparative method of the medication for treatment of addiction, the method comprises preparing the medication by mixing the active components, aconitane derivatives with anticholinergic agents as well as an excipient, or the mixing active component, aconitane derivatives with the excipient alone.

According to this invention, aconitane derivatives may be used together with anticholinergic agents to show better effect of treating addiction. In this invention, the anticholinergic agent used may be scopolamine, anisodamine, etc.

A preferred example of the medication to treat addiction from this invention is a composition of lappaconitine or its hydrobromide plus scoplamine as well as an excipient, or a composition of lappaconitine or its hydrobromide plus scoplamine hydrobromide as well as an excipient.

According to this invention, another preferred example of a medication to treat addiction from this invention is a composition of total alkaloids of A. sinomontanum or their hydrobromide plus scopolamine as well as an excipient, or a composition of total alkaloids of A. sinomontanum or their hydrobromide plus scopolamine hydrobromide as well as excipient.

According to this invention, the preferred example of the medication to treat addiction from this invention is a composition of N-deacetyllappaconitine or its hychobromide plus scopolamine as well as an excipient, or a composition of N-deacetyllappaconitine or its hydrobromide plus scopolamine hydropromide as well as an excipient.

According to this invention, the medication to treat addiction from this invention can be made to various preparation forms, such as tablets, powder, capsules or injections, etc. The preferred preparation form for this invention is the tablet form. The prescription of the tablet preferably contains 7 mg of lappaconitine hydrobromide, or N-deacetyl-lappaconitine hydrobromide, or the total alkaloids of A. sinomontanum hydrobromide, and 0.15 mg of scopolamine hydrobromide per tablet. The prescription of the injection preferably contains 6 mg~12 mg of lappaconitine hydrobromide and 0.15~0.3 mg of scopolamine hydrobromide per 1-2 ml ampule.

The next subject of this invention relates to method for treatment of addicts. The method involves administration of the medication from this invention to the addicts.

The administration route of the inventive medication can be oral, subcutaneous injection, intramuscular injection, intravenous injection, intravenous instillation, etc. According to this invention, the optimum route is oral administration. In the treatment according to the invention, the dosage is given as follows: For oral administration, during the first four days, a dose of 14 mg of lappaconitine hydrobromide plus 0.3 mg of scopolamine hydrobromide is given every 6 hr, 4 times a day; during the following 4 days, a dose of 7 mg of lappaconitine hydrobromide plus 0.15 mg of scopolamine hydrobromide is given every 8 hr, 3 times a day. If necessary, injection of 6~12 mg of lappaconitine hydrobromide plus 0.15~0.3 mg of scopolamine hydrobromide may be administered each time.

This invention can be demonstrated further with the following experiments which does not limit this invention in any way.

I. Addiction Test of Lappaconitine Hydrobromide

1. Mouse Jumping Test

Male mice weighting 18~22 g were used for the test and divided into 3 group of 10 mice each. The first group of mice was given a subcutaneous injection in a dose of 80 mg/kg morphine hydrochloride every day for 20 days. The second group of mice was given a subcutaneous injection of lappaconitine hydrobromide (8 mg/kg), and the injection lasted for 20 days. The third group was used as the physiological saline control group. 6 hr after being given the last dose, all the mice were given intraperitoneal injection of 10 mg/kg allyl dromaran, and then placed in a cone cylinder cage (diameter=30, height=35). The number of jumping mice within 60 min was recorded. The mice of the first group after administrating morphine looked excited, frequently run around and showed obvious pilo-erection reaction. The mice of the group showed obvious jumping reaction after injection of allyl dromaran. The mice of second group after administrating lappaconitine hydrobromide looked quiet and immobile, showed no pilo-erection reaction. After injection of allyl dromaran they showed no jumping reaction.

In another case, male mice weighting 18-22 g were divided into four groups of 10 mice each. Two groups of mice were injected subcutaneouly with lappaconitine hydrobromide 7 times within 2 days. The initial dosage was 3.5 mg/kg. Then, an additional dose of 0.5 mg/kg and 1.0 mg/kg was escalated for every injection in each group, respectively. The third group of mice was injected subcutaneously with morphine hydrochloride 7 times within 2 days. The initial dosage was 2.5 mg/kg and an escalating dose schedule (5, 10, 20, 30, 40, 50 mg/kg) was used. The fourth group of mice was the control of physiological saline. 2 hr after the last injection, all the mice of the above four groups were injected 50 mg/kg nalorphine through intraperitoneal cavity. The number of jumping within 10 minutes in various groups of mice were recorded. The obtained data was summaried in Tab. 3.

The test result listed is Tab. 3 showed that lappaconitine hydrobromide obviously differs from morphine hydrochloride, and the former does not cause drug dependence.

2. Substitution Test on Weight Reducing of morphine-dependent rats.

Wister male rats weighting 200-250 g were divided into 3 group of 10 rats each. All the three groups were given subcutaneous injection of 25 mg/kg morphine hydrochloride twice a day. The injection lasted for 12 weeks to cause rats dependence upon morphine. Discontinued injection of morphine, the rats looked suppressive and immobile, refusing food and losing weight (after 24 hr, the rats averagely losed weight of 25 g). Then the three groups of rats received injections of morphine, lappaconitine and physiological saline, respectively. The weight change of the rats was observed and recorded in FIG. 1.

BRIEF DESCRIPTION OF THE DRAWING

Note for FIG. 1:

Abscissa—24 hr after stopping injection of morphine for three groups of rats, the average weight change whthin 8 hr in each group of rats which were injected subcutaneously with morphine, lappaconitine and physiological saline, respectively.

Ordinate—The average weight lose in the three groups of rats at 24 hr after the injection of morphine was stopped, as well as the average weight change within 8 hr in each group which were given injection of morphine, physiological saline and lappaconitine, respectively 24 hr after stopping injection of morphine. In this case, the average weight before the stopping injection of morphine was proposed to be zero.

Figure 1:
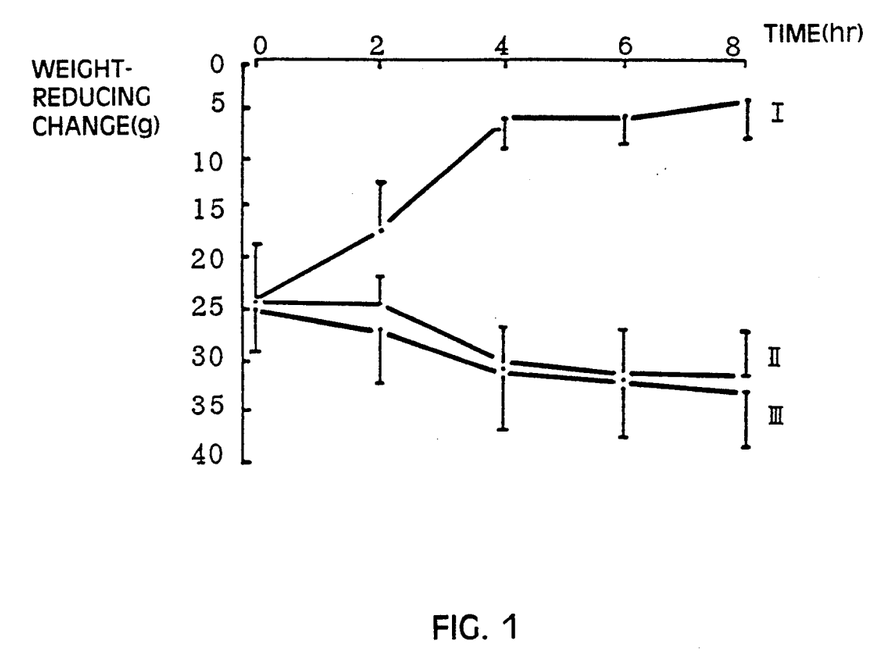

I: Morphine hydrochloride 25 mg/kg. SC
II: Physiological saline 2 ml/kg. SC
III: Lappaconitine hydrobromide 8 mg/kg. SC FIG. 1 showed which the group of rats which were injected with morphine turned from excited from being suppressive, moved increasingly, frequently took in food and water, and had a weight increase to the level before stopping injection of morphine. FIG. 1 also shows that the group of rats which were injected with lappaconitine looked still suppressive and had no weight increase. The test results indicate lappaconitine did not act as a substitution for morphine.

3. Monkey addiction test

Among 6 Macaca mulatta weighting 2.75~4.75 kg, three of the monkeys were subcutaneously injected lappaconitine twice a day. The initial dosage is 0.1 mg/kg, the dose was successively escalated to the maximum tolerance dosage, 2 mg/kg within 50 days. Then, the tolerance dosage was maintained to the day 53, day 67 and day 92, respectively. The total injection dosage for three monkeys was 196, 400 and 635 mg, respectively. On the day 63 and the day 92, the injection of lappaconitine was stooped to the monkeys. During the following 24 hr observation, the monkeys had no different behavior and appetite from that before stopping the injections. On the day 29, 53, 59, 67 and 90, the injections were discontinued and after 18 hr were given subcutaneous injection of nalorphine (4 or 8 mg/kg). No one showed withdrawal symptoms. Another three monkeys were given subcutaneous injection of morphine twice a day. The initial dosage was 2.5 mg/kg, and dosage was successively increased to 25 mg/kg on the day 21. Then, this dosage was maintained for the thirtieth day. By then, the monkeys exhibited dependence on morphine, 18 hr after stopping injection of morphine, the monkeys showed obvious withdrawal syndromes, such as agitation and restlessness, turning, lying on their side or in the bottom of the cage, scratching, biting their chain, crying, vomiting, shivering, paroxysmal tremol, etc. At that time, if a subcutaneous injection of morphine was given to the monkey, the above symptoms would be more obvious. 3-5 minutes after subcutaneous injection of morphine to the monkeys, the above withdrawal symptoms became obviously reduced or disappeared. A subcutaneous injection of 2 mg/kg lappaconitine could not relieve or weaken the above withdrawal symptoms. This indicates that lappaconitine has no action as a substitute for morphine. The above test result are listed in Table 4.

The above test results indicated that lappaconitine is different from morphine and does not cause dependence after long term use.

II. Toxicity Test

1. Acute Toxicity Test

Healthy mice weighting 18-22 g were a given toxicity dosage of lappaconitine through gasteria, subcutaneous injection and intravenous injection, and then exhibited toxicity reactions such as paroxysmal restlessness, foreleg tics. When given a lethal dosage, the mice showed paroxysmal convulsion, respiration suppression until suffocation, and death. The LD50 values (95% confidence limit) for i.g., in gasteria, subcutaneous injection and intravenous injection were 32.4 (25.9-40.5), 11.7 (9.2-14.9) and 8.4 (7.2-9.7) mg/kg, respectively. On being given an intraperitoneal injection of toxicity dosage of a lappaconitine, rats looked suppressive and immobile lying on their stomach in the cage, obvious suppression of respiration and showed convulsions before death. The LD50 was 16.5 (15.0–18.1) mg/kg.

Two Macca Mulatta were given subcutaneous injection of 2 mg/kg lappaconitine. No toxic reaction and no effect on electrocardiography was observed. 30 minutes after being given subcutaneous injection of 3 mg/kg lappaconitine, the monkeys showed the following signs and symptoms: restlessness, slobbering, swallow increasing, eyelids drooping, rigidity of legs muscle. After 45 minutes, one monkey increased restlessness, further developed convulsion. During convulsion, its respiration stopped, and recovered with artificial respiration, but still existed convulsion until death after 1 hr. Another monkey did not give any sign of convulsion, and the above toxic reaction lasted for 2 hr and disappeared. Electrocardiography examination indicated that T wave had elevation, T wave and P wave fused, and R wave became smaller and notching. Next day, the electrocardiography examination indicated the monkey being normal.

2. Subacute toxicity Test

Ten Wister rats weighting 200~250 g were divided into 2 groups of 5 rats each. Each group was given intraperitoneal injections of 5 mg/kg or 10 mg/kg of lappaconitine a day, respectively. The injection was continued for 30 days. 5 wister rats of control group were given subcutaneous injection of saline (2 ml/kg). Compared to the control group, the medicated group of rats showed inhibited weight increase at different levels. No obvious change was seen in an electrocardiography examination. No change was observed during the test of hepatic and renal function (GPT, Zinc sulfate turbity test, urea nitrogen, creatinine) and histological and pathological examinations of different viscera.

Another ten Wister rats were given successively escalated doses, in other words, the rats were first injected with lappaconitine (8 mg/kg) intraperitoneally, after one week, 10 mg/kg, after 2 weeks, 12 mg/kg, after 16 days, 14 mg/kg, and the last dose was maintained until the day 28. The test results indicated that the weight increase of the medicated group of rats inhibited less suppression, compared to the control group. The histological and pathological examinations of all viscera indicated similar results to the control group, except a little myocardial edema and hydropic degeneration.

3 Macca Mulatta weighting 2.75~4.75 kg were injected with lappaconitine subcutaneously twice a day. Initiated with 0.1 mg/kg, the dosage was increased successively to the highest tolerance dosage, 2 mg/kg within 50 days, and the last dosage was maintained to the day 53, day 67 and day 32, respectively. The accumulated injective dosage was 196,400 and 635 mg, respectively. No toxic reaction for monkeys was observed during the administration process. No obvious change appeared during the continuous electrocardiographic examination. Histological and pathological examinations mainly indicated a stimulating reaction, except a little edema and hydrodenaturation in the liver and increasing cerebral colloid cells.

III. A Treatment Test For Mice Dependent on Morphine or cocaine

Male mice weighting 18-22 g were injected subcutaneously morphine (100 mg/kg) twice a day, and the injection was continued for 8 days. 6 hours after the last dose, mice were injected with nalorphine (50 mg/kg) so that they showed frequent movement, attraction reaction and jumping reaction. The jumping reaction was most vigorous within 30 minutes. Based on the jumping reaction of the mice, those mice, whose jumping number was more than 60% of the average jumping number of 23 within 30 minutes, were selected (i.e. those mice whose average jumping number more than 14 were selected) and divided at random into 8 groups of 10 mice each.

As seven-day treatment to relieve morphine-dependence was conducted by utilizing the medications, the dose and administration route were listed in table 5 for each group of mice which exhibited morphine-dependence. Wherein the first 4 days, administration was made once per 6 hours, four times a day. From the days 5 through the day 7, administration was made once per 8 hours, three times a day. On the day 5 and the day 7 of treatment, subcutaneous injection of nalorphine (50 mg/kg) was given respectively to induce addiction. The test results indicated that each group of mice showed a negative reaction against nalorphine except that the control group of morphinedependent mice died mostly during seven days of subcutaneous injection of saline. The treatment was stopped and followed by 3-day observation. The mice treated did not produce withdrawal symptoms. Even with injecting nalorphine (50 mg/kg) subcutaneously, the mice did not show withdrawal symptoms.

The mice of the test group which was treated by the mecications containing lappaconitine or its derivatives respectively were compared with the morphine-dependent mice of the control group. The results showed that there exists a significant difference ($P<0.01$) between any one test group and the control group.

In the same way as described above, subcutaneous injection of cocaine (10 mg/kg) was given to the mice twice a day, and the injection was continued for 7 days. During this period of injection of cocaine, the mice gave abnormal signs such as anorexia, pilo-erection, and frequent walk with holding tail, etc. After treatment with lappaconitine, the mice recovered to normality.

IV. Clinic Treatment Test

Aged 20~35 years, ten drug addicts dependent on heroine or opium, whose duration of addiction ranged from 1 to 4 years were treated. Some of them have undergone treatment several times, but they failed. Before using the medication from this invention to treat addiction, all of the addicts were observed to have withdrawal symptoms such as yawing, sheding tears, chilliness, geting goose flesh, mydriasis, restlessness, etc., during the period of stopping drugs. The addicts were treated with the medication from this invention: in the first 4 days, oral administration of lappaconitine hydrobromide (14 mg/once), or total alkaloid of *A. sinopodopbyllym* hydrobromide (14 mg/once), or lappaconitine (14 mg once) plus scopolamine hydrobromide (0.3 mg once) was given four times per day; in next four days, the above medicine administration was given three times per day (in a half dosage). The clinic treatment result indicated that the withdrawal symptoms of the addicts became weakened on the day 3 after administration and on the day 4 and 5, the withdrawal symptoms disappeared totally. After said addicts were cured, withdrawal symptoms did not reappear. If the drug addicts were treated by injecting the medication of the invention, the treating process would be shortened.

The above test result demonstrated that the medication to treat addiction from this invention does not cause drug dependence. This medication has excellent effects to relieve drug dependence and to cure the withdrawal syndrome and acts rapidly without side effects.

TABLE 1

The relief medication substances (their inorganic acid salts included) for dependence - inductive drugs (opinium, morphlite, heroine, cocaine, marijuana, amphetamine, etc) and narcotics

| No. | aconitane derivatives | Formula | MW | mp (°C.) | Specific Rotation | $R_1$ | $R_2$ | $R_3$ | $R_4$ | $R_5$ | $R_6$ | R | Original Plant |
|---|---|---|---|---|---|---|---|---|---|---|---|---|---|
| 1 | Lappaconitine | $C_{32}H_{44}N_2O_8$ | 584 | 224–225 | $[\alpha]_D^{25}$ 27.0°(C0.22,CHCl$_3$) | OAcABz | H | OH | H | H | OCH$_3$ | αOCH$_3$ | A. conitum sinomontanum Nakai; A. finetianum Hand-Mazz |
| 2 | Lappaconine | $C_{23}H_{37}NO_6$ | 423 | 78–80 | | OH | H | OH | H | H | OCH$_3$ | αOCH$_3$ | A. finetianum Hand-Mazz |
| 3 | N-Deacetyllappaconitine | $C_{30}H_{42}N_2O_7$ | 542 | 117–119 | $[\alpha]_D^{33}$ 39.9°(C1.5,CHCl$_3$) | OABz | H | OH | H | H | OCH$_3$ | αOCH$_3$ | A. finetianum Hand-Mazz |
| 4 | Isolappaconitine | $C_{32}H_{44}N_2O_8$ | 584 | 198–200 | | OAcABz | OH | H | H | H | OCH$_3$ | αOCH$_3$ | A. finetianum Hand-Mazz |
| 5 | Deoxylappaconitine | $C_{32}H_{44}N_2O_7$ | 568 | 212–214 | | OAcABz | H | H | H | H | OCH$_3$ | αOCH$_3$ | A. finetianum Hand-Mazz |
| 6 | Neofinaconitine | $C_{30}H_{42}N_2O_6$ | 526 | | | OABz | H | H | H | H | OCH$_3$ | αOCH$_3$ | A. finetianum Hand-Mazz |
| 7 | Ranaconitine | $C_{32}H_{44}N_2O_9$ | 600 | 130–131 | $[\alpha]_D^{22}$ 40.2°(C0.19,MeOH) | OAcABz | OH | OH | H | H | OCH$_3$ | αOCH$_3$ | A. conitum sinomontanum Nakai; A. finetianum Hand-Mazz |
| 8 | Ranaconine | $C_{23}H_{37}NO_7$ | 439 | 105–107 | | OH | OH | OH | H | H | OCH$_3$ | αOCH$_3$ | A. finetianum Hand-Mazz |
| 9 | N-Deacetylranaconitine | $C_{30}H_{42}N_2O_8$ | 558 | 125–127 | $[\alpha]_D^{26}$ 43.7°(C2.0,CHCl$_3$) | OABz | OH | OH | H | H | OCH$_3$ | αOCH$_3$ | A. finetianum Hand-Mazz |
| 10 | Finaconitine | $C_{32}H_{44}N_2O_{10}$ | 616 | 220–221 | $[\alpha]_D^{22}$ 44.7°(C0.1.,MeOH) | OAcABz | OH | OH | OH | H | OCH$_3$ | αOCH$_3$ | A. finetianum Hand-Mazz |
| 11 | N-Deacetylfinaconitine | $C_{30}H_{42}N_2O_9$ | 574 | 121–123 | $[\alpha]_D^{10}$ 34.9°(C0.46,CHCl$_3$) | OABz | OH | OH | OH | H | OCH$_3$ | αOCH$_3$ | A. finetianum Hand-Mazz |
| 12 | Puberanine | $C_{32}H_{44}N_2O_9$ | 600 | | $[\alpha]_D^{20}$ 16.6°(C0.6,CHCl$_3$) | OAcABz | OH | OH | H | H | OCH$_3$ | βOCH$_3$ | A. barbatum var. puberulum |
| 13 | Episcopalisine | $C_{29}H_{39}NO_6$ | 497 | | $[\alpha]_D^{21}$ −11.7°(C3.2,EtOH) | H | H | OH | H | H | OBz | αOCH$_3$ | A. episcopale Le'vl |
| 14 | Episcopalisinine | $C_{22}H_{35}NO_5$ | 393 | 152–154 | $[\alpha]_D^{26}$ −8.7°(C6.8,EtOH) | H | H | OH | H | H | OH | αOCH$_3$ | A. episcopale Le'vl |
| 15 | Episcopalitine | $C_{24}H_{37}NO_5$ | 419 | | $[\alpha]_D^{22}$ −0.90°(C14.0,EtOH) | H | H | H | H | H | OAc | αOCH$_3$ | A. episcopale Le'vl |
| 16 | Delavaconitine | $C_{29}H_{39}NO_6$ | 497 | | $[\alpha]_D^{17}$ −9.56°(C7.0,EtOH) | H | H | H | H | OH | OBz | αOCH$_3$ | A. delavoyi Franch |
| 17 | Delavaconine | $C_{22}H_{35}NO_5$ | 393 | 152 | $[\alpha]_D^{15}$ −6.4°(C1.23,CHCl$_3$) | H | H | H | H | OH | OH | αOCH$_3$ | |
| 18 | Aconosine | $C_{22}H_{35}NO_4$ | 377 | 142–143 | $[\alpha]_D^{22}$ −25.4°(C4,MeOH) | H | H | H | H | H | OH | αOCH$_3$ | A. forentii Diels |
| 19 | Scopaline | $C_{21}H_{35}NO_4$ | 363 | 167–169 | | H | H | H | H | H | OH | αOH | A. episcopalo Le'vl |

AcABz = , ABz = —C(=O)—C$_6$H$_4$—NH$_2$, Ac = —COCH$_3$;

Bz = —C(=O)—C$_6$H$_5$

TABLE 2

The Relief medication substances (their inorganic acid salts included) for dependence - inductive drugs (opium, morphine, heroine, cocaine, marijuana, amphetamine, etc) and narcotics

| Name | formula | MW | mp (°C.) | Specific Rotation | $R_1$ | $R_2$ | $R_3$ | Original Plant |
|---|---|---|---|---|---|---|---|---|
| Aconine | $C_{25}H_{41}NO_9$ | 499 | 132 | $[\alpha]_D +23°$ | OH | OH | OH | |

II

TABLE 3

Observation of jumping reaction for mice after subcutaneous injections of lappaconitine or morphine

| Given pharmaceuticals | Dosage (mg/kg) | administration* (day) | Accumulated Total Dosage (mg/kg) | Number of mice Given pharmaceuticals | Tested | mg/kg Nalorphine | ip allyl dromaran | number of jumping mice | jumping times of each mouse |
|---|---|---|---|---|---|---|---|---|---|
| Physiological saline | — | 2 | | 10 | 10 | 50 | | 0 | 0 |
| | — | 20 | | 10 | 10 | | 10 | 0 | 0 |
| Morphine | 2.5 | 2 | 157.5 | 10 | 10 | 50 | | 7 | 9 |
| | 80 | 20 | 1600 | 10 | 10 | | 10 | 9 | 34 |
| Lappaconitine | 3.5 | 2 | 35 | 10 | 10 | 50 | | 0 | 0 |
| | 3.5 | 2 | 45.5 | 10 | 5** | 50 | | 0 | 0 |
| | 8.0 | 20 | 160 | 18 | 18 | | 10 | 1 | 0.2 |

*Once a day for 20 days group; Five times of injection on first day and twice on second day for 2 days group.
**During the administration of pharmaceuticals, five mice died of accumulated toxicity.

TABLE 4

Observation of the substitution role of lappaconitine in the withdrawal syndrome of morphine-dependent monkeys

| No. of monkey | Injection of morphine (day) | accumulated total dosage (g) | Withdrawal Syndrome 18 hr after stopping morphine | Nalorphine 0.5 mg/kg sc | Lappaconitine (2 mg/kg sc) |
|---|---|---|---|---|---|
| 6 | 42 | 4.66 | + | | − |
| 7 | 40 | 3.56 | + | | − |
| | 62 | 6.59 | | + | − |
| | 69 | 7.56 | | + | − |
| | 91 | 10.97 | + | | − |
| 8 | 33 | 3.61 | | + | − |
| | 49 | 6.06 | + | | − |

TABLE 5

Observation of treatment for Morphine-dependent Mice

| Medication | Dosage mg/kg (Administration route) | Days of Administration (time/hours) the Day 1-4 | the Day 5-7 | Accumulated Total Dosage (mg/kg) | Number of Mice Morphine-dependent | Treatment |
|---|---|---|---|---|---|---|
| Saline | 10 ml/kg (sc) | 1/6 | 1/8 | 250 ml | 10 | 8 |
| Lappaconitine hydrobromide | 0.45 (sc) | 1/6 | 1/8 | 11.25 | 10 | 10 |
| Lappaconitine hydrobromide* Scopolamine hydrobromide | 0.225 (sc) 0.05) (sc) | 1/6 | 1/8 | 5.63 | 10 | 10 |
| Lappaconitine hydrobromide Scopolamine hydrobromide | 0.45 0.1 (sc) | 1/6 | 1/8 | 11.2 2.5 | 10 | 10 |
| Lappaconitin hydrobromide Scopolamide hydrobromide | 0.9 0.2 (ig) | 1/6 | 1/8 | 22.5 5.0 | 10 | 10 |

TABLE 5-continued

| | | Observation of treatment for Morphine-dependent Mice | | | |
|---|---|---|---|---|---|
| | Dosage mg/kg | Days of Administration (time/hours) | | Accumulated Total | Number of Mice |
| Medication | (Administration route) | the Day 1-4 | the Day 5-7 | Dosage (mg/kg) | Morphine-dependent | Treatment |
| Lappaconitine hydrobromide | 0.45 | | | 11.25 | | |
| Scopolamide hydrobromide | 0.1 (ig) | 1/6 | 1/8 | 2.5 | 10 | 10 |
| N-deacetyllapp-aconitine hydrobromide | 5 (sc) | 1/6 | 1/8 | 125 | 10 | 10 |
| Lappaconine hydrobromide | 5 (sc) | 1/6 | 1/8 | 125 | 10 | 10 |

We claim:

1. A method to treat the withdrawal symptoms of narcotic addiction which comprises administering a withdrawal symptom effective amount of an aconitane derivative having the structures of formula I and II, inorganic acid salts therefore, or a mixture of two of the foregoing or In formula I, R=α—OCH$_3$, α—OH or β—OCH$_3$; R$_1$=OAcABz, OH, OABz or H; R$_2$=H or OH; R$_3$=H or OH; R$_4$=H or OH; R$_5$=H or OH$_3$; R$_6$=OCH$_3$, OBz, OAC or OH;

In formula II, R$_1$=R$_2$=R$_3$=OH and a pharmaceutically acceptable carrier to a patient.

2. A method according to claim 1, wherein the administration route includes oral administration, subcutaneous injection, intramuscular injection, intravenous injection or intravenous instillation.

3. A method according to claim 2, wherein the administration route is an oral administration.

4. A method according to claim 2, which comprises administration of total alkaloids *A. sinomontanum* or their inorganic acid salt to a patient.

5. A method according to claim 2, which comprises administrating mixture of total alkaloids of *A. sinomontanum* or their inorganic and salts with anticholinergic agents to a patient.

6. A method according to claim 2, which comprises administration of lappaconitine or its inorganic acid salts to a patient.

7. A method according to claim 2, which comprises administrating mixture of lappaconitine or its inorganic acid salts with anticholinergic agents to a patient.

8. A method according to claim 2, which comprises administration of N-deacetyl-lappaconitine or its inorganic acid salts to a patient.

9. A method according to claim 2, which comprises administrating mixture of N-deacetyl-lappaconitine or its inorganic acid salts with anticholinergic agents to a patient.

10. A method for the treatment of withdrawal symptoms of addiction to a drug selected from the group consisting of opium, morphine, heroin, cocaine, marijuana, and amphetamines which comprises administering a withdrawal symptom effective amount of an aconitane derivative having the structures of formula I and II, inorganic acid salts therefor, or a mixture of two of the foregoing wherein
R=α—OCH$_3$, α—OH, or β—OCH$_3$; R$_1$=OAcABz, OH, OABz, or H;
R$_2$=H or OH; R$_3$=H or OH; R$_4$=H or OH; R$_5$=H or OH$_3$;
R$_6$=OCH$_3$, OBz, OAc or OH; or wherein $R_1 = R_2 = R_3 = OH$ and a pharmaceutically acceptable carrier to a patient.

11. The method of claim 10 wherein the administration route includes oral administration, subcutaneous injection, intramuscular injection, intravenous injection or intravenous instillation.

12. The method of claim 10 wherein the administration route is an oral administration.

13. The method of claim 10 which comprises administration of total alkaloids *A. sinomontanum* or their inorganic acid salts to a patient.

14. The method of claim 10 which comprises administering a mixture of total alkaloids of *A. sinomontanum* or their inorganic acid salts with anticholinergic agents to a patient.

15. The method of claim 10 which comprises administration of lappaconitine or its inorganic acid salts to a patient.

16. The method of claim 10 which comprises administering a mixture of lappaconitine or its inorganic acid salts with anticholinergic agents to a patient.

17. The method of claim 10 which comprises administration of N-deacetyl-lappaconitine or its inorganic acid salts to a patient.

18. The method of claim 10 which comprises administering a mixture of N-deacetyl-lappaconitine or its inorganic acid salts with anticholinergic agents to patient.

* * * * *